United States Patent
Haupt et al.

(10) Patent No.: US 12,216,078 B2
(45) Date of Patent: Feb. 4, 2025

(54) ELECTROCHEMICAL FUEL CELL, PROCESS FOR MAINTAINING AN ELECTROCHEMICAL FUEL CELL AND BREATH ALCOHOL MEASURING DEVICE

(71) Applicant: Dräger Safety AG & Co. KGaA, Lübeck (DE)

(72) Inventors: Stephan Haupt, Lübeck (DE); Andreas Nauber, Lübeck (DE); Michael Sick, Lübeck (DE); Marie-Isabell Mattern-Frühwald, Lübeck (DE); Susanne Kassa, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 583 days.

(21) Appl. No.: 17/616,982

(22) PCT Filed: May 4, 2020

(86) PCT No.: PCT/EP2020/062298
§ 371 (c)(1),
(2) Date: Dec. 6, 2021

(87) PCT Pub. No.: WO2020/244860
PCT Pub. Date: Dec. 10, 2020

(65) Prior Publication Data
US 2022/0326177 A1    Oct. 13, 2022

(30) Foreign Application Priority Data

Jun. 7, 2019    (DE) .................... 10 2019 003 994.7

(51) Int. Cl.
*G01N 27/416*    (2006.01)
*A61B 5/00*    (2006.01)
(Continued)

(52) U.S. Cl.
CPC ......... *G01N 27/4163* (2013.01); *A61B 5/082* (2013.01); *A61B 5/4845* (2013.01);
(Continued)

(58) Field of Classification Search
CPC .............. G01N 27/4163; G01N 27/30; G01N 33/4972; G01N 33/0029; A61B 5/082
See application file for complete search history.

(56) References Cited

U.S. PATENT DOCUMENTS 3,509,034 A    4/1970    Harman
3,966,579 A *  6/1976    Chang ................ G01N 27/4045
                                                429/432
(Continued)

FOREIGN PATENT DOCUMENTS

CN    105993091 A    10/2016
DE    19619169 A1    11/1997
(Continued)

OTHER PUBLICATIONS

Mitzel et al., "Review on mechanisms and recovery procedures for reversible performance losses in polymer electrolyte membrane fuel cells," Journal of Power Sources 488 (2021) 229375 available online Jan. 12, 2021 (Year: 2021).*

(Continued)

*Primary Examiner* — Alexander S Noguerola
(74) *Attorney, Agent, or Firm* — McGlew and Tuttle, P.C.

(57) ABSTRACT

An electrochemical fuel cell measures ethanol in human breath and a process maintains such an electrochemical fuel cell. The electrochemical fuel cell includes a first electrode (1), a second electrode (2) and a third electrode (3). The first electrode (1) is used as a measuring electrode in a regular operating mode of the electrochemical fuel cell and as a measuring electrode or as a reference electrode in a maintenance mode of the electrochemical fuel cell. The second (Continued)

electrode (2) is used as a counter electrode in the regular operating mode of the electrochemical fuel cell and as a measuring electrode or as a reference electrode in the maintenance mode of the electrochemical fuel cell. The third electrode (3) is used as a counter electrode in the maintenance mode of the electrochemical fuel cell.

18 Claims, 1 Drawing Sheet

(51) Int. Cl.
*A61B 5/08* (2006.01)
*G01N 27/30* (2006.01)
*G01N 33/497* (2006.01)

(52) U.S. Cl.
CPC ......... *G01N 27/30* (2013.01); *G01N 33/4972* (2013.01); *A61B 2560/0223* (2013.01)

(56) References Cited

U.S. PATENT DOCUMENTS

| | | | | |
|---|---|---|---|---|
| 4,830,713 A | * | 5/1989 | Gagescu | G01N 27/38 204/402 |
| 5,759,368 A | * | 6/1998 | Kuhn | G01N 27/4045 205/785.5 |
| 5,932,079 A | | 8/1999 | Haupt et al. | |
| 5,944,661 A | * | 8/1999 | Swette | A61B 10/0064 600/362 |
| 9,057,691 B2 | | 6/2015 | Fodor et al. | |
| 2006/0130557 A1 | * | 6/2006 | Leddy | H01M 8/1039 73/23.3 |
| 2011/0091781 A1 | * | 4/2011 | Folmsbee | B60L 58/30 429/413 |
| 2016/0143561 A1 | * | 5/2016 | Egan, II | A61B 5/097 600/532 |
| 2017/0184537 A1 | | 6/2017 | Umasankar et al. | |
| 2019/0036136 A1 | | 1/2019 | Wolf et al. | |

FOREIGN PATENT DOCUMENTS

| | | | | |
|---|---|---|---|---|
| DE | 19622931 A1 | | 12/1997 | |
| EP | 1293778 A2 | | 3/2003 | |
| JP | 2009048940 A | | 3/2009 | |
| WO | WO 2014143175 A1 | * | 9/2014 | ........... G01N 27/404 |
| WO | 2019032119 A1 | | 2/2019 | |

OTHER PUBLICATIONS

EPO machine-generated English language translation of Jobst et al. EP 1293778 A1, patented Aug. 8, 2002 (Year: 2002).*

EPO machine-generated English language translaton of Haupt et al. DE 19622931 A1, patented Nov. 12, 1997 (Year: 1997).*

Easton et al. The application of power-generating fuel cell electrode materials and monitoring methods to breath alcohol sensors; Sensors and Actuators B: Chemical, (2016), 448-457.

* cited by examiner

ELECTROCHEMICAL FUEL CELL, PROCESS FOR MAINTAINING AN ELECTROCHEMICAL FUEL CELL AND BREATH ALCOHOL MEASURING DEVICE

CROSS REFERENCE TO RELATED APPLICATIONS

This application is a United States National Phase Application of International Application PCT/EP2020/062298, filed May 4, 2020, and claims the benefit of priority under 35 U.S.C. § 119 of German Application 10 2019 003 994.7, filed Jun. 7, 2019, the entire contents of which are incorporated herein by reference.

TECHNICAL FIELD

The present invention pertains to an electrochemical fuel cell for measuring ethanol in human breath, to a process for maintaining such an electrochemical fuel cell as well as to a fuel cell.

TECHNICAL BACKGROUND

The sensitivity of the cell to ethanol in the breath decreases steadily during the operation of an electrochemical fuel cell in a breath alcohol measuring device. This is due to different processes taking place on the surface of the catalyst layer. The sensitivity to alcohol becomes steadily lower, so that a calibration of the sensor with a known standard is necessary after a certain time. The alcohol measurement is a so-called relative method, in which the concentration is related to a standardized value, which is reached by the calibration with a known standard solution.

The electrochemical fuel cell is exposed time and time again to different substances from the environment and from the breath during the operation. This may lead over time to a poisoning/blocking of the surface. In addition, byproducts, which irreversibly cover absorption points on the surface of the catalyst layer and at which no oxidation of ethanol can take place any longer, are formed due to the oxidation of ethanol on platinum in the acid medium.

Calibration is carried out nowadays, as a rule, after a certain time in order to reach a predefined accuracy and to compensate the system-related deviation. However, this does not lead to an improvement of the sensitivity of the fuel cell, but only to an adaptation of the parameters. As an alternative or in addition, the fuel cell is replaced completely at regular time intervals. There also are other possibilities for increasing the stability of the fuel cell. The catalyst surface can be freed of adsorbates, for example, by electrochemical processes.

It is described in a scientific study of Easton et al. (Sensors & Actuators B: Chemical, 228 (2016), 448-457) that the reactivation of a catalyst surface of the platinum by means of a cyclical potential change can again increase the sensitivity of the surface to ethanol. However, it is not described how such a cyclical potential change can be implemented in an electrochemical fuel cell.

In addition, an attempt is made at increasing the sensitivity by making available a larger active oxidation surface (see, e.g., U.S. Pat. No. 9,057,691 B2).

SUMMARY

There is a need for an electrochemical fuel cell for a breath alcohol measuring device, in which the sensitivity to alcohol has a high stability.

The present invention is based on the discovery that a periodic renewal of a platinum oxide layer or platinum hydroxide layer of a platinum catalyst of the electrodes of an electrochemical fuel cell can be used to maintain the sensitivity of the electrodes for ethanol at a stable level over a longer time. In order to make it possible to carry out such a renewal, a third electrode (auxiliary electrode), which remains unused in a regular mode of operation of the fuel cell and which can be used as a counter electrode in a maintenance mode of the fuel cell, while one of the other two electrodes is used as a measuring electrode and the other as a reference electrode, is provided in a two-electrode fuel cell. The oxide or hydroxide layer of the platinum catalyst of the respective measuring electrode can be reduced to the metal in a first phase by applying a first potential. The polarization of the respective measuring electrode, which allows the formation of a new oxide or hydroxide layer, can take place in a second phase. The roles of the measuring electrode and of the reference electrode can then be transposed and the oxide or hydroxide layer of the other electrode can be regenerated.

Exemplary embodiments of the present invention provide an electrochemical fuel cell for measuring ethanol in human breath. The electrochemical fuel cell comprises a first electrode, a second electrode and a third electrode. The electrochemical fuel cell is characterized in that the first electrode is provided to be used (actuated and controlled/set) as a measuring electrode in a regular operating mode of the electrochemical fuel cell and as a measuring electrode or as a reference electrode in a maintenance mode of the electrochemical fuel cell. The electrochemical fuel cell is further characterized in that the second electrode is provided to be used (actuated and controlled/set) as a counter electrode in the regular operating mode of the electrochemical fuel cell and as a measuring electrode or reference electrode in the maintenance mode of the electrochemical fuel cell. The electrochemical fuel cell is further characterized in that the third electrode is provided to be used (actuated and controlled/set) as a counter electrode in the maintenance mode of the electrochemical fuel cell.

Due to the provision of the third electrode, which is used as a counter electrode in the maintenance mode, it is possible to regenerate the adsorption sites of the measuring electrode. This is made possible by the fact that a potential is generated in the maintenance mode. In order to make it possible to generate the potential, three electrodes are needed, namely, a measuring electrode and a counter electrode, between which a voltage is generated, and a reference electrode, which forms the reference point for the potential. If the potential is selected correctly, an oxide or hydroxide layer on the respective measuring electrode can be reduced at first and it can then be built up again, so that the oxide layer is renewed on the measuring electrode and the adsorption sites will be available again.

For example, with the electrochemical fuel cell as a two-electrode-based electrochemical fuel cell in the regular operating mode. The third electrode is provided (actuated and controlled/set) in this case to remain unused in the regular operating mode. This makes it possible to use the fuel cell as a two-electrode-based electrochemical fuel cell, which makes possible a high sensitivity and selectivity for ethanol and with which it is possible to avoid the need to take precautions against an instability of the reference electrode.

As an alternative, the electrochemical fuel cell may be a three-electrode-based electrochemical fuel cell in the regular operating mode. The third electrode may be provided in the regular operating mode for being used as a reference electrode. This makes it possible to use the present invention in three-electrode-based electrochemical fuel cells.

The electrochemical fuel cell comprises, furthermore, a control module in at least some exemplary embodiments. The control module may be configured to set a first potential of the measuring electrode against the reference electrode in a first phase of the maintenance mode. The control module may be further configured to set a second potential of the measuring electrode against the reference electrode in a second phase of the maintenance mode. The first potential may be selected now such that it leads to a reduction of an oxide or hydroxide layer at the respective measuring electrode. The second potential may be selected to be such that it leads to the build-up of the oxide or hydroxide layer at the respective measuring electrode.

For example, the first electrode and the second electrode may have a platinum surface. The first potential may be suitable for reducing a platinum oxide layer and/or a platinum hydroxide layer on the platinum surface of the first electrode or of the second electrode at least partially to platinum. The second potential may be suitable for regenerating a platinum oxide layer and/or a platinum hydroxide layer on the platinum surface of the first electrode or of the second electrode. Renewal of the oxide/hydroxide layer is made possible thereby.

The oxide/hydroxide layers of the first electrode and of the second electrode may be renewed in this case one after another, i.e., the roles (actuation and control/setting) of the two electrodes can be transposed within the maintenance mode. The maintenance mode may thus have a first time segment, which is provided for renewing a platinum oxide layer and/or a platinum hydroxide layer of the first electrode. The maintenance mode may further have a second time segment, which is provided for renewing a platinum oxide layer and/or a platinum hydroxide layer of the second electrode. The two time segments may comprise each the first phase and the second phase. This makes possible the renewal of the oxide/hydroxide layers of the first and second electrodes.

The first electrode may be provided and set for operation in this case to be used as a measuring electrode in the first time segment of the maintenance mode and as a reference electrode in the second time segment of the maintenance mode. The second electrode may be provided and set for operation for being used as a reference electrode in the first time segment of the maintenance mode and as a measuring electrode in the second time segment of the maintenance mode (or vice versa). The roles of the two electrodes are thus reversed within the maintenance mode.

The first time segment may take place chronologically before the second time segment, so that the oxide/hydroxide layer of the first electrode is renewed first and that of the second electrode is renewed thereafter. As an alternative, the second section may take place chronologically before the first time segment, so that the oxide/hydroxide layer of the second electrode is renewed first and that of the second electrode is renewed thereafter.

The duration of the first phase may be, for example, between 1 min and 10 min. Such a duration led to a successful reduction of the oxide/hydroxide layers in experiments.

The first potential may be, for example, between −400 mV and −700 mV. This corresponds to the voltage at which the platinum oxide/hydroxide layers are reduced to metal. The second potential may be between −100 mV and +100 mV. Oxide/hydroxide formation takes place on the electrodes at such a potential.

Further, exemplary embodiments create a process for maintaining an electrochemical fuel cell for measuring ethanol in human breath. The electrochemical fuel cell comprises a first electrode, a second electrode and a third electrode. The first electrode is provided to be used as a measuring electrode in a regular operating mode of the electrochemical fuel cell and as a measuring electrode or reference electrode in a maintenance mode of the electrochemical fuel cell. The second electrode is provided to be used as a counter electrode in the regular operating mode of the electrochemical fuel cell and as a measuring electrode or reference electrode in the maintenance mode of the electrochemical fuel cell. The third electrode is provided to be used as a counter electrode in the maintenance mode of the electrochemical fuel cell. The process comprises an operation of the electrochemical fuel cell alternatively in the regular operating mode or in the maintenance mode. The process comprises a setting, in a first phase of the maintenance mode, of a first potential of the measuring electrode against the reference electrode. The process further comprises, in a second phase of the maintenance mode, a second potential of the measuring electrode against the reference electrode.

Some examples of devices and/or processes will be explained as examples in more detail below. It is obvious that the present invention is not limited to these examples. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
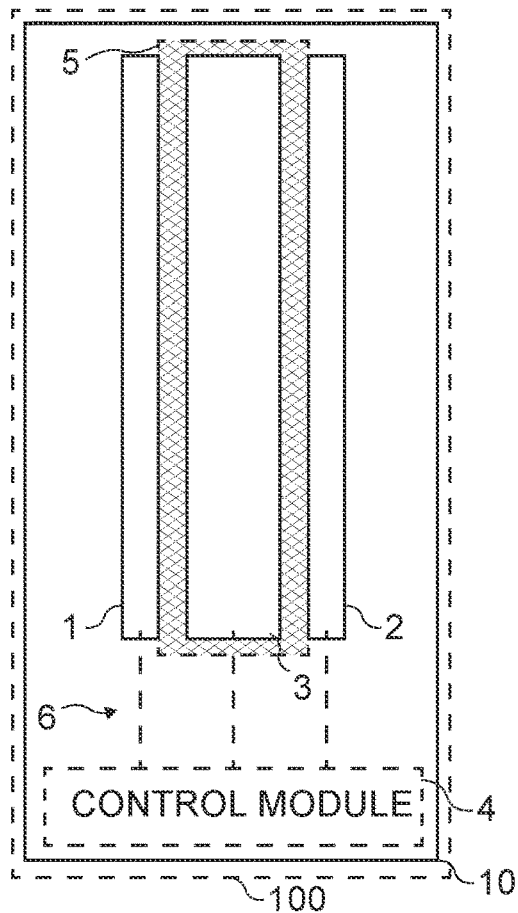
FIG. 1 is a schematic diagram of an electrochemical fuel cell for measuring ethanol in human breath.

Referring to the drawings, a thicknesses of lines, layers and/or areas may be exaggerated in the figures for illustration.

Further examples may cover all modifications, equivalents and alternatives, which fall within the scope of the disclosure. Identical or similar reference numbers pertain in the entire description of the figures to identical or similar elements, which may be implemented in an identical form or in a modified form in a comparison with one another, while they provide the same function or a similar function.

It is apparent that when an element is described as being "connected" to or "coupled" with another element, the elements may be connected or coupled directly or via one or more intermediate elements. When two elements A and B are combined with the use of an "or," this shall be understood to mean that all possible combinations are disclosed, i.e., only A, only B as well A and B, unless something else is explicitly or implicitly defined. An alternative formulation for the same combinations is "at least one of A and B" or "A and/or B." The same applies, mutatis mutandis, to combinations of more than two elements.

The terminology that is used here to describe specific examples shall not represent a limitation for other examples. If a singular form, e.g., "a" and "the" is used and the use of only a single element is not defined as being obligatory either explicitly or implicitly, further examples may also use plural elements in order to implement the same function. When a function is described below as being implemented with the use of a plurality of elements, further examples may implement the same function with the use of an individual element or of an individual processing entity. It is further obvious that the terms "comprises," "comprising," "has" and/or "having" specify, when used, the presence of the indicated features, integers, steps, operations, processes, elements, components and/or a group thereof, but they do not rule out the presence of the addition of one or more other features, integers, steps, operations, processes, elements, components and/or a group thereof.

Unless defined otherwise, all terms (including technical and scientific terms) are used here in their usual meaning in the field to which the examples belong.

FIG. 1 shows a schematic diagram of an electrochemical fuel cell 10 for measuring ethanol in human breath. The electrochemical fuel cell comprises a first electrode 1, a second electrode 2 and a third electrode 3. As is shown in FIG. 1, the fuel cell further comprises an electrolyte, which is stored in the exemplary embodiment shown in FIG. 1 in a membrane 5, which is arranged between the first electrode and the second electrode. The third electrode is arranged, furthermore, at the membrane with the electrolyte, i.e., the first electrode, the second electrode and the third electrode are in contact with the same electrolyte. The third electrode may alternatively be coupled to the test cell with the first electrode and with the second electrode via an electrolyte bridge. Other arrangements are, in principle, may also be provided, but the present invention pertains to the interaction of the three electrodes. This is characterized by the first electrode 1 being provided to be used as a measuring electrode in a regular operating mode of the electrochemical fuel cell and as a measuring electrode or as a reference electrode in a maintenance mode of the electrochemical fuel cell. The second electrode 2 is provided to be used as a counter electrode in the regular operating mode and as a measuring electrode or reference electrode in the maintenance mode of the electrochemical fuel cell. The third electrode 3 is provided to be used as a counter electrode in the maintenance mode of the electrochemical fuel cell. FIG. 1 further shows a breath alcohol measuring device 100 comprising the electrochemical fuel cell 10.

As can be determined from the above description, the present invention is based on the three electrodes having different operation settings for different tasks in the regular operating mode and in the maintenance mode. The regular operating mode is an operating mode of the electrochemical fuel cell in which a breath alcohol test can be carried out, e.g., with the use of a coulometric method. The maintenance mode is an operating mode that is provided for a renewal of oxide or hydroxide layers on the catalyst layers on the electrodes.

The first electrode 1 is provided to be used as a measuring electrode in a regular operating mode and as a measuring electrode or reference electrode in a maintenance mode of the electrochemical fuel cell. The regular operating mode is controlled in this case, for example, by a control module 4, which may (logically) be comprised by the electrochemical fuel cell itself (the fuel cell control). The control module may be configured to operate the electrochemical fuel cell either in the regular operating mode or in the maintenance mode. Further modes may likewise be possible, e.g., a calibration mode or a standby mode. In order to make it possible to change over between the regular operating mode and the maintenance mode, the control module may be configured to adapt a wiring structure 6, which connects the electrodes electrically to the control module, corresponding to the particular use of the electrodes. The wiring structure may be comprised by the control module 4, i.e., it may be a microelectronic wiring structure. As an alternative, the wiring structure may comprise one or more relays, which can be controlled by the control module 4. The control module may be configured, for example, to control the wiring structure such that the first electrode is operated as a measuring electrode in the regular operating mode and as a measuring electrode or as a reference electrode in the maintenance mode of the electrochemical fuel cell.

The control module 4 may correspondingly be configured to control the wiring structure 6 such that the second electrode 2 is operated as a counter electrode in the regular operating mode of the electrochemical fuel cell and as a measuring electrode or reference electrode in the maintenance mode of the electrochemical fuel cell. The control module may further be configured to control the wiring structure 6 such that the third electrode 3 is operated as a counter electrode in the maintenance mode of the electrochemical fuel cell. The control module may further be configured to control the wiring structure 6 such that the third electrode 3 remains unused in the regular operating mode, i.e., so that the third electrode is switched off and/or so that the electrochemical fuel cell is operated without the third electrode. The electrochemical fuel cell 10 may thus be a two-electrode-based electrochemical fuel cell (without reference electrode) in the regular operating mode. The control module may be configured to control the wiring structure 6 such that third electrode 3 is provided to remain unused in the regular operating mode. As an alternative, the control module may be configured to control the wiring structure 6 such that the third electrode 3 is used as a reference electrode in the regular operating mode. The electrochemical fuel cell 10 can thus be, for example, a three-electrode-based electrochemical fuel cell in the regular operating mode. The third electrode 3 may be provided in the regular operating mode to be used as a reference electrode.

Breath alcohol measuring devices that comprise an electrochemical fuel cell are usually recalibrated at regular intervals in order to provide conclusive results. A main reason for the regular calibration of such devices is the mode of operation of the fuel cell. The concentration of the breath alcohol is determined by the ethanol in the breath and other constituents of the breath leading at the measuring electrode of the electrochemical fuel cell to a so-called poisoning/blockage of the surface of a catalyst of the measuring electrode, i.e., adsorption sites on the catalyst of the measuring electrode in question are occupied by the substances and they will not thereafter be available for the oxidation of ethanol on the catalyst surface. This oxidation of the catalyst is, however, the basis for the alcohol measurement in such breath alcohol measuring devices, because the oxidation of ethanol leads to a flow of electrons in the fuel cell, which can be measured and which is proportional to the concentration of the breath alcohol. If the oxidation of ethanol is made difficult by the unavailability of the adsorption sites, the sensitivity (i.e., the conversion factor) can be adapted in the subsequent calculation of the breath alcohol content, so that the measured value corresponds to the breath alcohol content. This adaptation is comprised in the calibration of the breath alcohol measuring device.

The present invention is based on the discovery that it is possible to regenerate the adsorption sites by applying a potential to the measuring electrode, with which potential an oxide or hydroxide layer of the catalyst will first be decomposed and then built up again. This regeneration takes place during the maintenance mode. In other words, the maintenance mode is provided to renew (i.e., first decompose and then regenerate) an oxide or hydroxide layer of a catalyst of the respective measuring electrode. This potential may be generated in exemplary embodiments by the control module. The control module may be comprised by the electrochemical fuel cell (outside an electrolyte space, i.e., logically associated with the electrochemical fuel cell and electrically connected to the electrodes). The control module may be comprised in this case by a microcontroller, which comprises the electrochemical fuel cell. Where exactly the control module is arranged is irrelevant as long as it is logically associated with the electrochemical fuel cell.

The control module 4 may consequently be configured to set a potential in the electrochemical fuel cell. A potential of a measuring electrode in an electrochemical fuel cell should always be seen in relation to the reference electrode, i.e., the potential is a potential difference between the potential of the reference electrode and the potential of the measuring electrode. The reference electrode is in this case operated (controlled/set) as an electrode (if possible), which is not subject to a current load, so that a constant potential is present at the reference electrode. The potential at the measuring electrode can be set, for example, via a so-called potentiostatic control circuit, a circuit in which a flow of current is generated between the measuring electrode and the counter electrode in order to set the potential. The control module may comprise, for example, a potentiostatic control circuit or another control circuit, which is configured to set the potential. The control module may further be configured to carry out a measurement of a current between the measuring electrode and the counter electrode during the regular operating mode. The current curve is proportional in this case to the breath alcohol (the ethanol in the breathing air), and it can be used in a next processing step to determine the breath alcohol.

The control module may be configured, for example, to set in a first (chronological and/or logical) phase of the maintenance mode a first potential of the measuring electrode in relation to the reference electrode (i.e., to set the first potential at the measuring electrode, wherein the first potential is set in relation to the reference electrode). The first potential may be selected in this case such that it is suitable for reducing an oxide layer and/or a hydroxide layer on a surface of a catalyst layer, which is arranged on the surface of the measuring electrode, to metal, i.e., to induce a reduction, in which the oxygen and/or the hydrogen are released. Such a potential is reached when the decomposition voltage is exceeded (or is undershot, when this is negative). The first electrode 1 and the second electrode 2 may have a platinum surface in an example of an exemplary embodiment, i.e., the measuring electrode has in the maintenance mode a platinum surface that can act as a catalyst surface in the regular operating mode. The first potential may be suitable for reducing a platinum oxide layer and/or a platinum hydroxide layer on the platinum surface of the first electrode 1 or of the second electrode 2 at least partially to platinum. The first potential may be in this case between −400 mV and −700 mV (e.g., between −500 mV and −600 mV). The first phase may last a few minutes, e.g., between 1 minute and 10 minutes, but also longer, even if no or only a slighter additional reduction can then be expected. The duration of the first phase may be about at least one minute, at least two minutes, at least three minutes or at least five minutes.

The control module may further be configured to set a second potential of the measuring electrode against the reference electrode in a second (chronological and/or logical) phase of the maintenance mode (i.e., to set the second potential at the measuring electrode, wherein the second potential is set in relation to the reference electrode). The second phase may be carried out after the first phase. The second potential may be selected to be such that it is suitable for allowing the formation of an oxide layer and/or of a hydroxide layer on a surface of a catalyst layer, which is arranged on the surface of the measuring electrodes. For example, the second potential may be suitable for regenerating a platinum oxide layer and/or a platinum hydroxide layer on the platinum surface of the first electrode 1 or of the second electrode 2. The second potential may correspond to a polarization potential, i.e., the potential may be formed by the elements counteracting during an electrolysis. In other words, a polarization of the measuring electrode and of the counter electrode may take place during the second phase. The control module may be configured in this case to allow the formation of the second potential by polarization of the electrodes (i.e., not to provide itself for a current flow, which leads to a potential). As an alternative, the control module may be configured actively to set the second potential, e.g., such that the second potential is between −100 mV and +100 mV, e.g., so that the oxide or hydroxide layer can be regenerated. A transition between the first potential and the second potential may in this case take place gradually, i.e., the control module may be configured to bring about a gradual transition between the first potential and the second potential.

Not only the oxide or hydroxide layer of a single electrode is regenerated in the maintenance mode in at least some exemplary embodiments, but the oxide/hydroxide layers of both the first electrode and of the second electrode can be regenerated as well. The maintenance mode may comprise for this two time segments, which comprise the first phase and the second phase, respectively. In other words, the maintenance mode may have a first time segment, which is provided for renewing a platinum oxide layer and/or a platinum hydroxide layer of the first electrode 1. The first electrode 1 may be provided for this purpose for being used as a measuring electrode in the first time segment of the maintenance mode and as a reference electrode in the second time segment of the maintenance mode. The maintenance mode may further have a second time segment, which is provided for renewing a platinum oxide layer and/or a platinum hydroxide layer of the second electrode 2. The second electrode 2 may be provided (controlled and set) for being used as a reference electrode in the first time segment of the maintenance mode and as a measuring electrode in the second time segment of the maintenance mode.

The two time segments may comprise each the first phase and the second phase. For example, the oxide/hydroxide layer on the surface of the catalyst of the first electrode can be reduced to metal in the first phase of the first time segment, and the oxide/hydroxide layer on the surface of the catalyst of the first electrode can be regenerated in the second phase of the first time segment. The oxide/hydroxide layer on the surface of the catalyst of the second electrode can be reduced to metal in the first phase of the second time segment, and the oxide/hydroxide layer on the surface of the catalyst of the second electrode can be regenerated in the second phase of the second time segment. The designations "first" time segment and "second" time segment in some exemplary embodiments do not represent a chronological sequence, i.e., the first time segment may take place chronologically before the second time segment, or the second time segment may take place chronologically before the first time segment.

The control module 4 may correspond in exemplary embodiments to any desired controller or processor or to a programmable hardware component. For example, the control module 4 may also be embodied as software, which is programmed for a corresponding hardware component. The control module 4 may thus be implemented as programmable hardware with correspondingly adapted software. Any desired processors, such as digital signal processors (DSPs) may be used in this case. Exemplary embodiments are not limited to a specific type of processor. Any desired processors or even a plurality of processors may also be provided for the implementation of the control module 4.

More details and aspects of the electrochemical fuel cell or of the breath alcohol measuring device will be mentioned in connection with the concept or examples, which were described before or will be described later (e.g., FIG. 2). The electrochemical fuel cell or the breath alcohol measuring device may comprise one or more additional optional features, which correspond to one or more aspects of the concept being proposed or to the examples described, as they were described above or will be described below.

Figure 2:
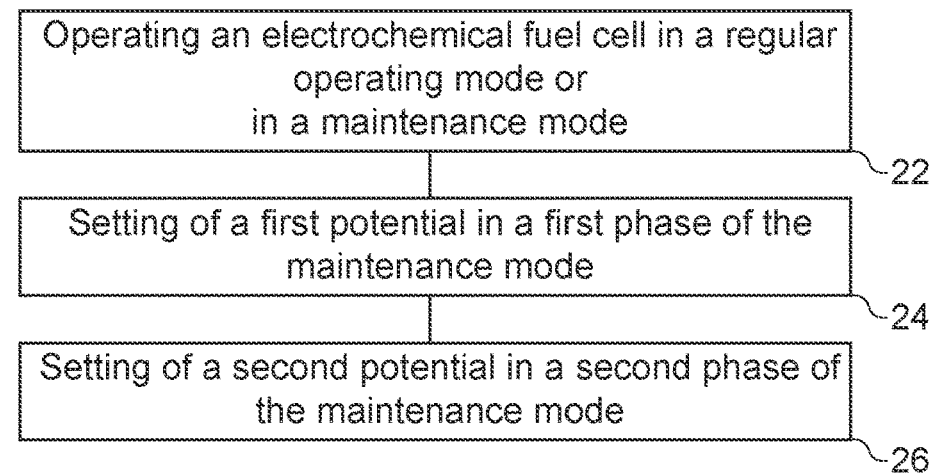
FIG. 2 is a flow chart of a process for maintaining an electrochemical fuel cell for measuring ethanol in human breath.

FIG. 2 shows a flow chart of a corresponding process 20 for maintaining an electrochemical fuel cell for measuring ethanol in human breath. The process may be carried out, for example, by an electrochemical fuel cell 10 and/or by the breath alcohol measuring device 100 according to FIG. 1. The electrochemical fuel cell comprises a first electrode, a second electrode and a third electrode. These may have configurations similar to those of the electrodes of the electrochemical fuel cell according to FIG. 1. Thus, the first electrode is provided for being used as a measuring electrode in a regular operating mode of the electrochemical fuel cell and as a measuring electrode or reference electrode in a maintenance mode of the electrochemical fuel cell. The second electrode is provided for being used as a counter electrode in the regular operating mode of the electrochemical fuel cell and as a measuring electrode or reference electrode in the maintenance mode of the electrochemical fuel cell. The third electrode is provided for being used as a counter electrode in the maintenance mode of the electrochemical fuel cell.

The process comprises an operation 22 of the electrochemical fuel cell alternatively in the regular operating mode or in the maintenance mode. The electrochemical fuel cell may comprise for this purpose, for example, a control module, which is configured to operate the electrochemical fuel cell alternatively in the regular operating mode or in the maintenance mode, i.e., the operation of the electrochemical fuel cell in the regular operating mode or in the maintenance mode can be brought about by the control module 4.

The process further comprises a setting 24, in a first phase of the maintenance mode, of a first potential of the measuring electrode against the reference electrode. The process further comprises a setting 26, in a second phase of the maintenance mode, of a second potential of the measuring electrode against the reference electrode. The setting of the potentials may be carried out similarly to what was described in connection with FIG. 1.

The maintenance mode may, moreover, have two time segments, a first time segment and a second time segment. The first time segment may be provided for renewing an oxide layer (e.g., a platinum oxide layer) and/or a hydroxide layer (e.g., a platinum hydroxide layer) of the first electrode. The second time segment may be provided for renewing an oxide layer (e.g., a platinum oxide layer) of the second electrode. The two time segments may comprise each the first phase and the second phase. In other words, the process may comprise the carrying out of a renewal of an oxide layer and/or of a hydroxide layer of the first electrode by carrying out the first phase and the second phase in a first time segment. The process may comprise the carrying out of a renewal of an oxide layer and/or of a hydroxide layer of the second electrode by carrying out the first phase and the second phase in a second time segment. A sequence of the time segments may be selected as desired, i.e., the first time segment may take place chronologically before the second time segment, or the second time segment may take place chronologically before the first time segment.

More details and aspects of the process will be mentioned in connection with the concept or examples, which were described above or will be described later (e.g., FIG. 1). The process may comprise one or more additional optional features, which correspond to one or more aspects of the concept being proposed or of the examples described, as they were described above or will be described later.

At least some exemplary embodiments create a process for regenerating the catalyst surface of a fuel cell (e.g., electrochemical fuel cell according to FIGS. 1 and/or 2) for increasing the sensitivity to breath alcohol with the use of a temporarily connected auxiliary electrode (of the third electrode).

Breath alcohol measuring devices are used worldwide. These devices frequently contain an electrochemical fuel cell for measuring the ethanol content in the breath. The breath alcohol concentration of a test subject can be determined by the use of the coulometric method if the quantity of the sample is known exactly. The devices are also exposed at times to other substances (organic compounds in the breath, cigarette smoke, etc.), in addition to the target gas ethanol. The fuel cell can be recalibrated for this reason at regular time intervals against a known ethanol standard in order to continue to meet the specified requirements. A calibration interval of 3-12 months is selected in most cases in order to guarantee the highest possible accuracy of the measuring system.

The present invention pertains to a process, in which the electrochemical fuel cell, which is used to measure the ethanol in the human breath, can be regenerated by a temporarily connected electrode such that the electrochemical catalyst surface will gain react highly selectively and sensitively to ethanol.

Exemplary embodiments thus also create an electrochemical fuel cell (two-electrode sensor with measuring electrode and counter electrode) for measuring breathing alcohol, with an additional third electrode, which is used (only) during the regeneration of the measuring electrode and/or counter electrode.

Byproducts of the oxidation of alcohol as well as other substances may be absorbed from the ambient air on the platinum surface of the counter electrode and the measuring electrode during the operation of the sensor in the device. Furthermore, an oxide layer or a hydroxide layer, which may influence the reaction of alcohol, is formed on the platinum surfaces. The surfaces of the measuring electrode and of the counter electrode can be regenerated by the platinum oxide or platinum hydroxide layers being reduced electrochemically to the metal and being subsequently formed anew.

The sensitivity to ethanol can be increased again by the regeneration of the electrochemical sensor, so that long calibration intervals can be obtained in some embodiments.

Irreversible adsorption of byproducts as a consequence of the oxidation of ethanol and changes in the oxide and hydroxide layer on the surface of the catalyst lead, among other things, to a reduction of the sensitivity of the sensor. The calibration is in some systems the only means of maintaining the accuracy of the sensor for ethanol after a certain operating time. A temporarily connected auxiliary electrode can renew the oxide layer by means of a regenerative process and remove adsorbed species from the surface. The stability of the sensitivity can be markedly increased by a fuel cell with an additional, temporarily connected auxiliary electrode by regeneration of the catalyst layer. This makes it possible to prolong the service life and hence also to improve the stabilization of the electrochemical system.

To regenerate the counter electrode, the sensor is switched over, for example, from the two-electrode operation to the three-electrode operation. The electrode, which acts as a measuring electrode in the two-electrode operation, is used as a reference electrode. The counter electrode is operated as a measuring electrode and the additional third auxiliary electrode is used as a counter electrode. A potential, at which the platinum oxide or hydroxide on the surface is reduced to the metal, is set on the counter electrode used as a measuring electrode in the regular operating mode over a time period of 1-10 minutes. The oxide or hydroxide layer is built up again subsequently by polarization to 0 mV or even to other potentials (e.g., −50 mV, +75 mV, etc., against the reference electrode). The third auxiliary electrode is then switched off again and the sensor continues to be operated for the further measurement of alcohol as a fuel cell with two electrodes.

To regenerate the measuring electrode, the sensor is switched over from the two-electrode operation to the three-electrode operation. The electrode, which acts as a counter electrode in the two-electrode operation, is used as a reference electrode. The measuring electrode continues to be operated as a measuring electrode and the additional third auxiliary electrode is used as a counter electrode. A potential, at which the platinum oxide or hydroxide on the surface is reduced to the metal, is set at the measuring electrode over a time period of 1-10 minutes. The oxide or hydroxide layer is then built up again by polarization to 0 mV or even to other potentials (e.g., −50 mV, +75 mV, etc., against the reference electrode). The third auxiliary electrode is then switched off again and the sensor continues to be operated as a fuel cell with two electrodes for the further measurement of alcohol.

During the operation in the device, the system can be operated as a prior-art fuel cell system with high sensitivity and selectivity for ethanol. The auxiliary electrode (3rd electrode) is not operated permanently in the case of a two-electrode system contrary to all other amperometric systems.

Calibration may, furthermore, be carried out at regular timer intervals, because a regular comparison with a standard should be carried out. The cell will, however, remain stable over a markedly longer time period in exemplary embodiments.

The present disclosure is focused on the activity of the platinum electrode and on the recovery of sensitivity.

As an alternative, the measuring electrode of a three-electrode alcohol sensor can be regenerated as well. A potential, at which the platinum oxide or hydroxide on the surface is reduced to the metal, is set at the measuring electrode over a time period of 1-10 minutes. The oxide or hydroxide layer is then built up again by polarization to 0 mV or even to other potentials (e.g., −50 mV, +75 mV, etc., against the reference electrode).

The aspects and features, which are described together with one or more of the examples and figures described above in detail, may also be combined with one or more of the other examples in order to replace an identical feature of the other example or in order to additionally introduce the feature into the other example.

It is apparent that the disclosure of a plurality of steps, processes, operations or functions disclosed in the description or in the claims shall not be interpreted as being in a defined sequence, unless this is stated explicitly or implicitly otherwise, e.g., for technical reasons. Therefore, these are not limited by the disclosure of a plurality of steps or functions to a defined sequence, unless these steps or functions are not replaceable for technical reasons. Further, an individual step, function, process or operation may include a plurality of partial steps, partial functions, partial processes or partial operations and/or be broken up into these. Such partial steps may be included and be a part of the disclosure of this individual step, unless they are explicitly ruled out.

Furthermore, the following claims are herewith included in the detailed description, in which each claim may represent a separate example in itself. While each claim may stand as a separate example in itself, it should be noted that, even though a dependent claim may refer in the claims to a certain combination with one or more other claims, other examples may also comprise a combination of the dependent claim with the subject of every other dependent or independent claim. Such combinations are proposed here explicitly unless it is stated that a certain combination is not provided. Further, features of a claim may also be included for each other independent claim, even if this claim is not made directly dependent on the independent claim.

While specific embodiments of the invention have been shown and described in detail to illustrate the application of the principles of the invention, it will be understood that the invention may be embodied otherwise without departing from such principles.

The invention claimed is:

1. An electrochemical fuel cell for measuring ethanol in human breath, the electrochemical fuel cell comprising:
    a first electrode;
    a second electrode;
    a third electrode, wherein
        the first electrode is provided as a measuring electrode in a regular operating mode of the electrochemical fuel cell and as a measuring electrode or reference electrode in a maintenance mode of the electrochemical fuel cell,
        the second electrode is provided as a counterelectrode in the regular operating mode of the electrochemical fuel cell and as a measuring electrode or reference electrode in the maintenance mode of the electrochemical fuel cell, and
        the third electrode is provided as a counterelectrode in the maintenance mode of the electrochemical fuel cell; and
    a control module operatively connected to the first electrode, to the second electrode and to the third electrode and configured to control the first electrode, the second electrode and the third electrode to operate the electrochemical fuel cell alternatively in the regular operating mode or in the maintenance mode, to set, in a first phase of the maintenance mode, a first potential of one of the first electrode and the second electrode operating as the measuring electrode relative to another one of the first electrode and the second electrode operating as the reference electrode, and to set, in a second phase of the maintenance mode, a second potential of the one of the first electrode and the second electrode operating as the measuring electrode relative to the another one of the first electrode and the second electrode operating as the reference electrode.

2. The electrochemical fuel cell in accordance with claim 1, wherein the electrochemical fuel cell is operated as a two-electrode-based electrochemical fuel cell in the regular operating mode based on the first electrode as the measuring electrode and the second electrode as the counterelectrode, wherein the third electrode is provided to remain unused in the regular operating mode.

3. The electrochemical fuel cell in accordance with claim 1, wherein the electrochemical fuel cell is operated as a three-electrode-based electrochemical fuel cell in the regular operating mode, wherein the third electrode is provided and operated in the regular operating mode as a reference electrode.

4. The electrochemical fuel cell in accordance with claim 1,
wherein the first electrode and the second electrode have a platinum surface,
wherein the first potential is suitable for reducing a platinum oxide layer and/or a platinum hydroxide layer on the platinum surface of the first electrode or of the second electrode at least partially to platinum, and
wherein the second potential is suitable for regenerating a platinum oxide layer and/or a platinum hydroxide layer on the platinum surface of the first electrode or of the second electrode.

5. The electrochemical fuel cell in accordance with claim 1,
wherein the maintenance mode has a first time segment, which is provided for renewing a platinum oxide layer and/or a platinum hydroxide layer of the first electrode, and
wherein the maintenance mode has a second time segment, which is provided for renewing a platinum oxide layer and/or a platinum hydroxide layer of the second electrode, and
wherein the two time segments comprise each the first phase and the second phase.

6. The electrochemical fuel cell in accordance with claim 5,
wherein the first electrode is operated as a measuring electrode in the first time segment of the maintenance mode and as a reference electrode in the second time segment of the maintenance mode, and
wherein the second electrode is operated as a reference electrode in the first time segment of the maintenance mode and as a measuring electrode in the second time segment of the maintenance mode.

7. The electrochemical fuel cell in accordance with claim 5, wherein the first time segment takes place chronologically before the second time segment, or wherein the second time segment takes place chronologically before the first time segment.

8. The electrochemical fuel cell in accordance with claim 1, wherein the duration of the first phase is between 1 minute and 10 minutes.

9. The electrochemical fuel cell in accordance with claim 1,
wherein the first potential is between −400 mV and −700 mV, and/or
wherein the second potential is between −100 mV and +100 mV.

10. A breath alcohol measuring device comprising an electrochemical fuel cell, the electrochemical fuel cell comprising:
a first electrode provided as a measuring electrode in a regular operating mode of the electrochemical fuel cell and as a measuring electrode or reference electrode in a maintenance mode of the electrochemical fuel cell;
a second electrode provided as a counterelectrode in the regular operating mode of the electrochemical fuel cell and a measuring electrode or reference electrode in the maintenance mode of the electrochemical fuel cell;
a third electrode provided as a counterelectrode in the maintenance mode of the electrochemical fuel cell; and
a control module operatively connected to the first electrode, to the second electrode and to the third electrode and configured to control the first electrode, the second electrode and the third electrode to operate the electrochemical fuel cell alternatively in the regular operating mode or in the maintenance mode, to set, in a first phase of the maintenance mode, a first potential of one of the first electrode and the second electrode operating as the measuring electrode relative to another one of the first electrode and the second electrode operating as the reference electrode, and to set, in a second phase of the maintenance mode, a second potential of the one of the first electrode and the second electrode operating as the measuring electrode relative to the another one of the first electrode and the second electrode operating as the reference electrode.

11. The breath alcohol measuring device in accordance with claim 10, wherein the electrochemical fuel cell is operated as a two-electrode-based electrochemical fuel cell in the regular operating mode based on the first electrode as the measuring electrode and the second electrode as the counterelectrode, wherein the third electrode is provided to remain unused in the regular operating mode.

12. The breath alcohol measuring device in accordance with claim 10, wherein the electrochemical fuel cell is operated as a three-electrode-based electrochemical fuel cell in the regular operating mode, wherein the third electrode is provided and operated in the regular operating mode to be used as a reference electrode.

13. The breath alcohol measuring device in accordance with claim 10, wherein:
the first electrode and the second electrode have a platinum surface,
the first potential is suitable for reducing a platinum oxide layer and/or a platinum hydroxide layer on the platinum surface of the first electrode or of the second electrode at least partially to platinum, and
the second potential is suitable for regenerating a platinum oxide layer and/or a platinum hydroxide layer on the platinum surface of the first electrode or of the second electrode.

14. The breath alcohol measuring device in accordance with claim 13, wherein:

the maintenance mode has a first time segment, which is provided for renewing a platinum oxide layer and/or a platinum hydroxide layer of the first electrode; and the maintenance mode has a second time segment, which is provided for renewing a platinum oxide layer and/or a platinum hydroxide layer of the second electrode, and the two time segments comprise each the first phase and the second phase.

15. The breath alcohol measuring device in accordance with claim 14, wherein:

the first electrode is operated as a measuring electrode in the first time segment of the maintenance mode and as a reference electrode in the second time segment of the maintenance mode; and the second electrode is operated as a reference electrode in the first time segment of the maintenance mode and as a measuring electrode in the second time segment of the maintenance mode.

16. The breath alcohol measuring device in accordance with claim 10, wherein the duration of the first phase is between 1 minute and 10 minutes.

17. The breath alcohol measuring device in accordance with claim 10, wherein the first potential is between −400 mV and −700 mV, and/or the second potential is between −100 mV and +100 mV.

18. A process for maintaining an electrochemical fuel cell for measuring ethanol in human breath, wherein the electrochemical fuel cell comprises a first electrode, a second electrode, a third electrode and a control module operatively connected to the electrodes and configured to control the electrodes, wherein the first electrode is provided to be used as a measuring electrode in a regular operating mode of the electrochemical fuel cell and as a measuring electrode or as a reference electrode in a maintenance mode of the electrochemical fuel cell, wherein the second electrode is provided to be used as a counterelectrode in the regular operating mode of the electrochemical fuel cell and as a measuring electrode or as a reference electrode in the maintenance mode of the electrochemical fuel cell, wherein the third electrode is provided to be used as a counterelectrode in the maintenance mode of the electrochemical fuel cell, the process comprising:

operating, with the control module, the electrochemical fuel cell alternatively in the regular operating mode or in the maintenance mode, setting, with the control module in a first phase of the maintenance mode, a first potential of one of the first electrode and the second electrode operating as the measuring electrode relative to another one of the first electrode and the second electrode operating as the reference electrode; and setting, with the control module in a second phase of the maintenance mode, a second potential of the one of the first electrode and the second electrode operating as the measuring electrode relative to the another one of the first electrode and the second electrode operating as the reference electrode.

* * * * *